US008947525B2

(12) United States Patent
Moon et al.

(10) Patent No.: US 8,947,525 B2
(45) Date of Patent: Feb. 3, 2015

(54) PLANT OBSERVATION DEVICE AND METHOD

(75) Inventors: Ae Kyeung Moon, Daegu (KR); Kyuhyung Kim, Daegu (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 322 days.

(21) Appl. No.: 13/616,989

(22) Filed: Sep. 14, 2012

(65) Prior Publication Data

US 2013/0113924 A1    May 9, 2013

(30) Foreign Application Priority Data

Nov. 4, 2011    (KR) .......................... 10-2011-0114664

(51) Int. Cl.

| G01J 1/00 | (2006.01) |
| G01J 1/02 | (2006.01) |
| G01J 1/42 | (2006.01) |
| G01N 21/25 | (2006.01) |
| G01J 5/08 | (2006.01) |
| G06F 17/30 | (2006.01) |
| G01N 21/63 | (2006.01) |

(52) U.S. Cl.
CPC .............. *G01J 1/0219* (2013.01); *G01J 1/4204* (2013.01); *G01N 21/25* (2013.01); *G01J 5/0846* (2013.01); *G01N 2021/635* (2013.01)
USPC .......................................... 348/135; 356/213

(58) Field of Classification Search
USPC .......................................... 348/135; 356/213
See application file for complete search history.

(56) References Cited

U.S. PATENT DOCUMENTS

| 5,130,545 A * | 7/1992 | Lussier ...................... 250/458.1 |
| 7,836,072 B2 * | 11/2010 | Yoneda ......................... 707/770 |
| 2006/0076048 A1 * | 4/2006 | Gaudiana et al. ............. 136/246 |
| 2007/0012349 A1 * | 1/2007 | Gaudiana et al. ............. 136/244 |
| 2011/0135161 A1 * | 6/2011 | Koutsky et al. .............. 382/110 |
| 2013/0308675 A1 * | 11/2013 | Sneed et al. .................. 374/121 |
| 2014/0250778 A1 * | 9/2014 | Suntych .......................... 47/1.4 |

FOREIGN PATENT DOCUMENTS

| JP | 2004-16182 | 1/2004 |
| KR | 10-0699162 | 3/2007 |
| KR | 10-0929476 | 12/2009 |
| KR | 1020100000626 | 1/2010 |
| KR | 1020110065129 | 6/2011 |

* cited by examiner

*Primary Examiner* — Sath V Perungavoor
*Assistant Examiner* — Howard D Brown, Jr.
(74) *Attorney, Agent, or Firm* — Nelson Mullins Riley & Scarborough LLP

(57) ABSTRACT

A plant observation device measures the growing state of a plant placed in a measurement area and the growth environment in the measurement area while moving within the measurement area where the plant is cultivated. The quantity of light is measured during growth environment measurement, and a light transmitting state of the measurement area is detected based on the measured quantity of light and the time of light quantity measurement. The measured growing state information and growth environment information are transmitted, together with positional information, to a server of a remote monitoring system. The growth environment in the measurement area is then optimally controlled based on the growing state information and the growth environment information.

20 Claims, 7 Drawing Sheets

PLANT OBSERVATION DEVICE AND METHOD

CROSS-REFERENCE TO RELATED APPLICATION

This application claims priority to and the benefit of Korean Patent Application No. 10-2011-0114664 filed in the Korean Intellectual Property Office on Nov. 4, 2011, the entire contents of which are incorporated herein by reference.

BACKGROUND OF THE INVENTION (a) Field of the Invention

The present invention relates to a plant observation device and method, and more particularly, to a device and method for observing the growth of plants.

(b) Description of the Related Art

To cultivate plants, glass greenhouses or plastic greenhouses are widely used. The inside of a greenhouse is kept at a higher temperature than the outside by solar heating, and most of the solar light passes through glass or plastic and is transmitted to plant bodies, thereby creating a very favorable environment for the growth of plants.

The environmental control of greenhouses needs to be varied depending on developmental stages or growing states of plants, degree of disease and pest incidence, etc. Thus, growth information of plants in greenhouses is the most important factor for determining the level of control. Therefore, for automatic control of greenhouse environments, it is necessary to collect plant growth information (e.g., leaf temperature, leaf moisture, internode length, sclerocauly, chlorophyll content, number of flower sets, number of fruit sets, fruit color, etc.), as well as climatic environment conditions, such as temperature, humidity, etc. in greenhouses.

In general, a method of measurement with the naked eye has been used to observe the growth of plants, growth speed thereof, and so on. Plants grow the most in the summer when sunlight is plentiful. If the weather is very changeable, it is difficult to forecast the total yield for that year, and therefore it is difficult to predict types and amounts of plants for export and types and amounts of imported plants. Moreover, although it is necessary to accurately measure the growth of plants in upcountry regions so as to make observations of plant growth and accurate predictions of yields depending on weather changes, there is no means to accurately measure it at every moment, and this causes the inconvenience of someone having to make observations themselves. Accordingly, there are difficulties in observing and storing accurate plant growth data.

Moreover, problems such as inconsistencies in observation time and limits to the frequency of observation arise in observing the growing state of cultivated plants with human eyes, and there is a high probability of data errors in measurement because a human observer makes a measurement while touching the plants with their hands. Also, a lot of time is spent measuring plant growth information, and there are many inconveniences when exchanging information with researchers or management organizations, and thus measurements are hardly used as research data, thereby making it difficult to predict the total yield for a year.

To solve these problems, a system was disclosed in which plants are observed by zooming in or out on them with an image capture device mounted on the ceiling of a greenhouse. However, this system is incapable of making accurate measurements of the actual growing state of a plant because of the distance between the image capture device and the plant.

Further, a ubiquitous management system, etc. were developed in which sensors nodes for measuring growth environment factors of plants are installed in an area or greenhouse where the plants are produced, the growing state of the plants is monitored using the sensor nodes, collected current state information is transmitted to a mobile terminal through local wireless communication, and the inside of the greenhouse is controlled according to a control signal generated from the mobile terminal.

However, these systems have limitations in measuring the growing state of a plant more accurately because the growing state of the plant is measured by the sensors nodes installed at fixed positions.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a device and method for measuring information more accurately and conveniently on a growing state and growth environment of plants.

Furthermore, the present invention has been made in an effort to provide a device and a method for adaptively measuring the growing state of a plant depending on the plant's growth speed.

An exemplary embodiment of the present invention provides a plant observation device including: a plant growing state measurement unit that measures the growing state of a plant to acquire growing state information; a growth environment measurement unit that measures the growth environment of a measurement area in which the plant is cultivated to acquire growth environment information, measures the quantity of light of the measurement area, and detects a light transmitting state of the measurement area based on the measured quantity of light and the time of light quantity measurement; and a transmission unit that transmits the measured growing state information and growth environment information of the plant, and additionally transmits positional information of each location where the growing state information and growth environment information are acquired, wherein the plant observation device observes a plant placed at a given location while moving within the measurement area.

The plant growing state measurement unit may include: an image capture unit that captures an image of a plant; and a capture position adjusting unit that acquires the size of the plant from the captured image of the plant and adjusts the position of the image capture unit based on the acquired size of the plant. The size of the plant may represent the length of the plant, and the image capture unit may be adjusted to a position corresponding to the tip of the plant.

The growth environment measurement unit may further include at least one of: a light quantity measuring unit for measuring the quantity of light in the measurement area; a temperature measuring unit for measuring the temperature in the measurement area; a humidity measuring unit for measuring the humidity in the measurement area; and a carbon dioxide measuring unit for measuring the concentration of carbon dioxide in the measurement area.

The light quantity measuring unit may include: a light quantity measuring module for measuring the quantity of light at a given location of the measurement area; a solar position estimation module for estimating a current solar position based on the time of light quantity measurement; a threshold value setting module for setting a threshold value for an optimum quantity of light at the light quantity measurement location based on the estimated solar position; and a detection module for comparing the threshold value with the measured quantity of light.

If the current measured quantity of light is lower than the threshold value, it is detected that a defect in the quantity of light has occurred at the corresponding location, and the detection module may transmit positional information of the measurement area with the defect and defect code information indicating the occurrence of defective light transmission at the corresponding location.

Another embodiment of the present invention provides a plant observation method, including: acquiring, by a plant observation device, growing state information by measuring a growing state of a plant placed in a measurement area while moving within the measurement area; creating, by the plant observation device, growth environment information by measuring the growth environment in the measurement area while moving within the measurement area; and transmitting, by the plant observation device, a status message containing the measured growing state information and growth environment information of the plant and positional information of the measurement area where the information is acquired, wherein the creating of growth environment information includes measuring the quantity of light in the measurement area, and detecting a light transmitting state of the measurement area based on the measured quantity of light and the light quantity measurement time.

The acquiring of growing state information may include: causing the image capture unit to capture an image of the plant; acquiring the size of the plant from the captured image of the plant; adjusting the position of the image capture unit based on the acquired size of the plant so that the image capture unit is placed in a position corresponding to the tip of the plant; and causing the position-adjusted image capture unit to capture an image of the plant and acquiring the growing state information based on the captured image.

The detecting of a light transmitting state may further include: measuring the quantity of light at a given location of the measurement area; estimating the current solar position based on the time of light quantity measurement; setting a threshold value for an optimum quantity of light at the light quantity measurement location based on the estimated solar position; comparing the threshold value with the measured quantity of light; and if the measured quantity of light is lower than the threshold value, detecting that a defect in the quantity of light has occurred at the light quantity measurement location.

The creating of growth environment information may further include at least one of: measuring the temperature in the measurement area; measuring the humidity in the measurement area; and measuring the concentration of carbon dioxide in the measurement area.

Yet another embodiment of the present invention provides a plant observation method including: acquiring, by a plant observation device, an image of a plant placed in a measurement area while moving within the measurement area; detecting the presence or absence of a pest from the image of the plant; if there is a pest, performing observation and diagnosis of the pest; and transmitting a result of the observation and diagnosis and positional information of the plant from which the pest is detected.

The performing of the observation and diagnosis of the pest may include at least one of: identifying the type of the pest; measuring the density of the pest population in the plant; making a record of times of pest detection and measuring the incidence of pests indicative of the frequency with which a pest occurs based on the record of times of pest detection; acquiring images of surrounding plants placed within a set distance from the plant from which the pest is found; modifying a plant image acquisition cycle; and transmitting a pest diagnosis result and positional information of the plant from which the pest is detected.

DETAILED DESCRIPTION OF THE EMBODIMENTS

Figure 1:
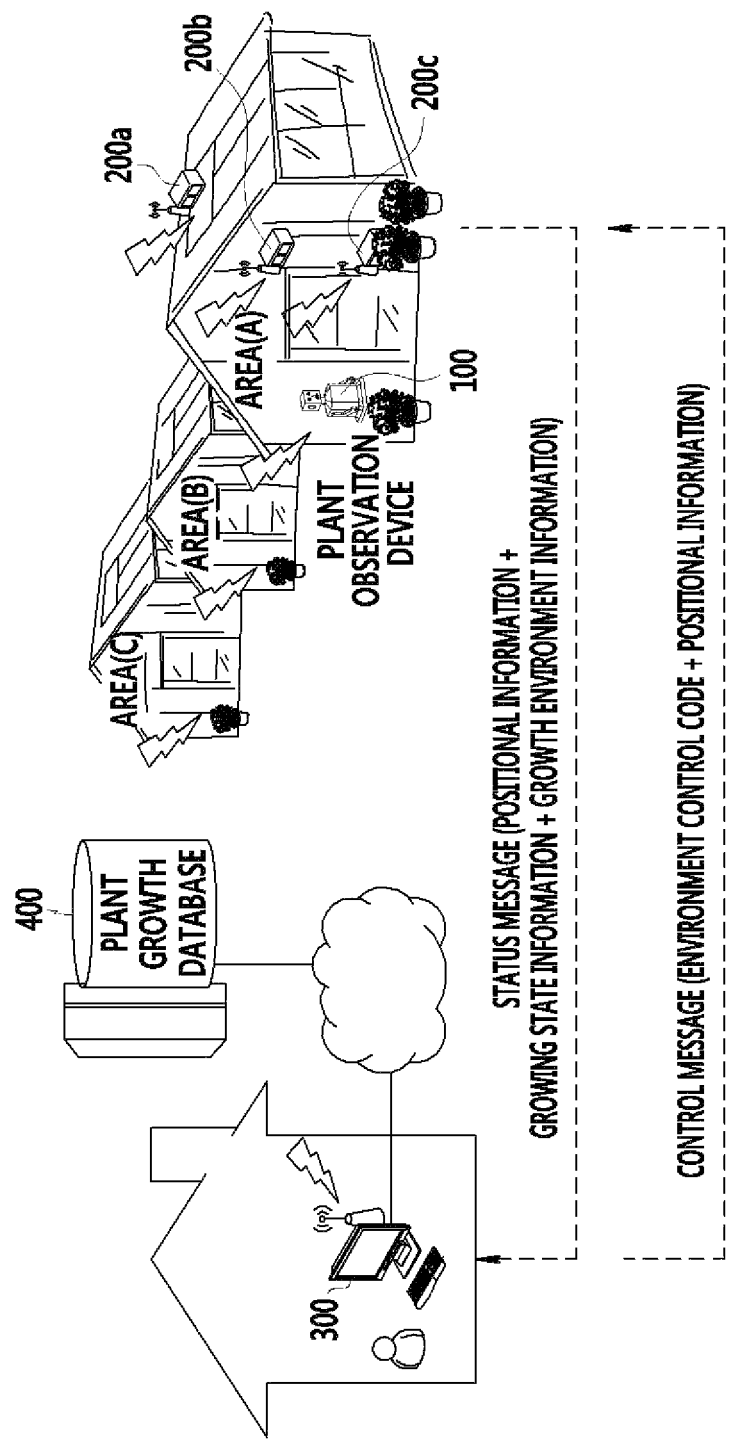
FIG. 1 is a view showing a growing state monitoring system using a plant observation device according to an exemplary embodiment of the present invention.

In the following detailed description, only certain exemplary embodiments of the present invention have been shown and described, simply by way of illustration. As those skilled in the art would realize, the described embodiments may be modified in various different ways, all without departing from the spirit or scope of the present invention. Accordingly, the drawings and description are to be regarded as illustrative in nature and not restrictive. Like reference numerals designate like elements throughout the specification.

Throughout the specification, unless explicitly described to the contrary, the word "comprise" and variations such as "comprises" or "comprising" will be understood to imply the inclusion of stated elements but not the exclusion of any other elements.

FIG. 1 is a view showing a growing state monitoring system using a plant observation device according to an exemplary embodiment of the present invention.

As shown in FIG. 1, the plant growing state monitoring system according to the exemplary embodiment of the present invention includes a plant observation device 100, a plurality of controllers (e.g., 200a, 200b, and 200c), an environment control server 300, and a plant growth database 400.

Although FIG. 1 illustrates one plant observation device 100 and three controllers 200a, 200b, and 200c for one measurement area A for convenience of explanation, the number of plant observation devices and the number of controllers installed in one area may vary. That is, more than one plant observation device and more than one controller may be installed in one area. Also, the number of plant observation devices or the number of controllers installed for each area may vary. Here, it is assumed that the same numbers of plant observation devices and controllers as in the area A are installed in other areas B and C.

The plant observation device 100 measures the growing state or growth environment of plants while moving within a measurement area, and transmits measured growing state information or growth environment information to the environment control server 300. Herein, the plant observation device 100 can also transmit positional information of the measurement location. That is, the plant observation device 100 measures the growing state of a plant cultivated, for example, in the area A, and creates a status message containing measured plant growing state information and positional information of the location where the measurement is made and transmits it to the environment control server 300. Also, the plant observation device 100 measures the growth environment of a plant cultivated, for example, in the area A, and creates a status message containing measured plant growth environment information and positional information of the location where the measurement is made and transmits it to the environment control server 300. The positional information contained in the status message may be at least one of the following: information on the location of a measurement area, information on the location where growing state measurement information is acquired, and information on the location where growth environment measurement information is acquired.

The controllers 200a, 200b, and 200c are mechanisms that control the environmental conditions of a measurement area, especially ones that operate in accordance with a control message transmitted from the environment control server 300 or the plant observation device 100, and control the environmental conditions of a measurement area.

For example, the controller 200a, which is a mechanism that controls the opening and closing of a ventilation window, i.e., a skylight window, fixed on the ceiling of a greenhouse corresponding to the measurement area A, controls the opening and closing of the ventilation window fixed on the ceiling of the greenhouse according to the control of the environment control server 300. The controller 200b is installed in the measurement area A, and controls temperature in accordance with a control message from the environment control server 300. The controller 200c is installed in the measurement area A, and controls humidity in accordance with a control message from the environment control server 300. These functions of the controllers are only examples, and various functions for changing the conditions of a plant growth environment may be additionally used.

The controllers 200a, 200b, and 200c each store positional information indicating the positions where they are installed. The positional information stored in the controllers 200a, 200b, and 200c may be central position information of the measurement area, or the installation positions of the controllers 200a, 200b, and 200c.

The environment control server 300 receives a status message directed to the plant observation device 100 to collect plant growing state information of the measurement area and growth environment information of the measurement area. The collected plant growing state information or growth environment information is stored in the plant growth database 400 at the data center via a wireless network. The plant growth database 400 can be managed by the data center.

Moreover, the environment control server 300 analyzes the collected plant growing state and growth environment information of the measurement area, determines the level of control of environmental factors in the measurement area, and creates an environment control code, i.e., instruction code, according to the determined level of control of environmental factors. Also, the control server 300 broadcasts a control message containing the environment control code. Positional information of the plant observation device 100 may be contained in the control message.

The controllers 200a, 200b, and 200c receive the broadcasted control message, compare the positional information contained in the control message and their own stored positional information, and if the positional information is consistent, perform environmental control in accordance with the environment control code contained in the control message. Also, the plant observation device 100 may receive the broadcasted control message, compare the positional information contained in the control message and its own stored positional information, and if the positional information is consistent, transmit the environment control code to a controller conforming to the environment control code contained in the control message so that the controller performs appropriate environmental control in accordance with the environment control code transmitted from the environment control server 300. Hereupon, the controllers 200a, 200b, and 200c themselves may receive the control message from the environment control server 300 and perform environmental control, or the plant observation device 100 may receive the control message and operate the controllers 200a, 200b, and 200c in accordance with the control message.

Figure 2:
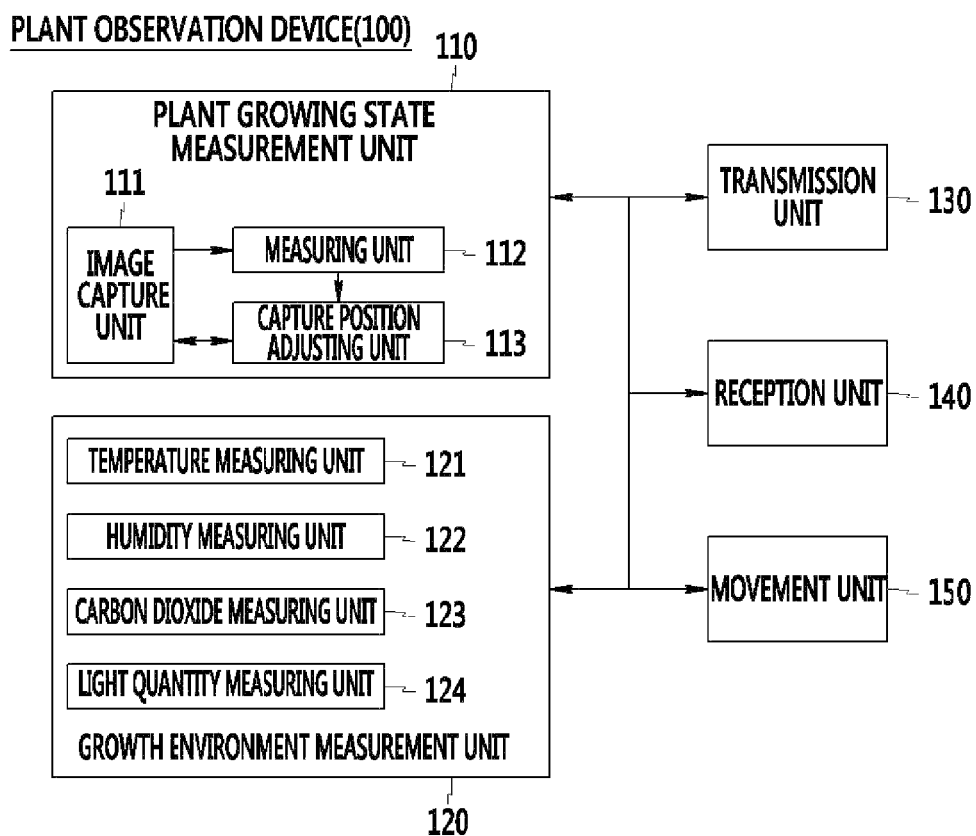
FIG. 2 is a view showing a structure of a plant observation device according to an exemplary embodiment of the present invention.

FIG. 2 is a view showing a structure of a plant observation device according to an exemplary embodiment of the present invention.

As shown in FIG. 2, the plant observation device 100 according to the exemplary embodiment of the present invention includes a plant growing state measurement unit 110, a growth environment measurement unit 120, a transmission unit 130, and a reception unit 140, and is movable. The plant observation device 100 according to the exemplary embodiment of the present invention measures the growing state and growth environment of plants while moving. To this end, the plant observation device 100 further includes a movement unit 150 that moves the plant observation device 100 in accordance with a set movement algorithm or dynamically moves it depending on a measured surrounding environment.

The plant growing state measurement unit 110 measures the growing state of a plant disposed in a measurement area. The growing state of plants includes, but not limited to, leaf temperature, leaf moisture, internode length, sclerocauly, chlorophyll content, number of flower sets, number of fruit sets, fruit color, etc., and may include all growing states of plants that can be measured in the art.

The plant growing state measurement unit 110 according to the exemplary embodiment of the present invention includes an image capture unit 111 for capturing an image of a plant and a measuring unit 112 for measuring the growing state of the plant based on the captured image of the plant. It further includes a capture position adjusting unit 113 for adjusting the position of the image capture unit 111 based on the size of the plant acquired from the captured image of the plant.

The capture position adjusting unit 113 measures the size of the plant, for example, a plant length equal to the length from the surface of the ground to the tip of the plant, based on the captured image of the plant, and measures the position of the image capture unit 111 based on the measured plant length. For example, the image capture unit 111 is placed in a position corresponding to the tip of the plant based on the measured plant length. By adjusting the position of the image capture unit 111, a plant is captured at an optimum position depending on the growing state of the plant, whereby the growing state of the plant is measured more accurately.

The plant growing state measurement unit 110 according to the exemplary embodiment of the present invention also performs diagnosis of diseases and pests of plants. For example, it detects the presence or absence of a pest based on captured images of the plants. Also, it can measure the incidence of pests indicative of the frequency with which each type of pest occurs according to the detected presence or absence of the pest and the type of the pest. The allowable level of disease and pest damage can be determined based on type and density of disease and pest, transfer status of disease and pest, weather conditions, plant growing state, and so on. Proper means for control of the plants can be determined based on a result of the diagnosis of diseases and pests. The determined means for control may be transmitted to the environment control server 300 or a mobile terminal (not shown) of the administrator through the transmission unit 130. In some cases, the plant observation device 100 according to the exemplary embodiment of the present invention may perform control itself.

In the exemplary embodiment of the present invention, the plant observation device 100 is capable of taking close-up images of plants while moving, thereby measuring the state of the plants more accurately. Based on close-up images rather than images taken at a far distance, more accurate diagnosis of diseases and pests can be achieved. Accordingly, a disease and pest diagnosis process requiring periodic checks can be performed more accurately and reliably, and data obtained by the disease and pest diagnosis can be used for more effective management of plants.

Meanwhile, the growth environment measurement unit 120 measures the growth environment of a measurement area. To this end, the growth environment measurement unit 120 includes a temperature measuring unit 121 for measuring temperature, a humidity measuring unit 122 for measuring humidity, a carbon dioxide measuring unit 123 for measuring the concentration of carbon dioxide, and a light quantity measuring unit 124 for measuring the quantity of light. However, the growth environment measurement unit 120 is not limited thereto, and may further include means for measuring other growth environments of plants that can be measured in the art.

Particularly, the light quantity measuring unit 124 according to the exemplary embodiment of the present invention measures the quantity of light for each given location, and detects any defect in the light transmission of the measurement area corresponding to a light quantity measurement location by taking the measured quantity of light and the current solar position into consideration. For example, in the case the measurement area is a greenhouse, the light quantity measuring unit 124 detects a defect in glass that does not allow an appropriate quantity of light to pass and enter the greenhouse, i.e., a light quantity measurement location. Concretely, after the light quantity measurement is carried out, the solar position is estimated based on the current time, a threshold value for the quantity of light to be measured at the light quantity measurement location based on the estimated current solar position is compared with the current measured quantity of light. If the current measured quantity of light is lower than the threshold value, it is determined that the light transmitting state at the current light quantity measurement location is defective.

Figure 3:
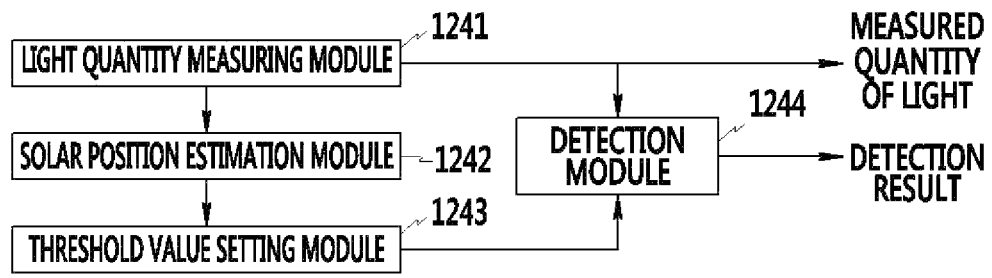
FIG. 3 is a view showing a structure of a light quantity measuring unit of a plant observation device according to an exemplary embodiment of the present invention.

To this end, the light quantity measuring unit has such a structure as shown in FIG. 3.

FIG. 3 is a view showing a structure of a light quantity measuring unit according to an exemplary embodiment of the present invention.

As shown in FIG. 3, the light quantity measuring unit 124 according to the exemplary embodiment of the present invention includes a light quantity measuring module 1241 for measuring the quantity of light at a given location, a solar position estimation module 1242 for estimating the current solar position based on the time of light quantity measurement, a threshold value setting module 1243 for setting a threshold value for an optimum quantity of light at the light quantity measurement location based on the estimated solar position, and a detection module 1244 for detecting a defect by comparing the threshold value with the measured quantity of light.

If any defect is detected, the transmission unit 130 may later transmit a status message which contains positional information of the measurement area with the defect (e.g., the location of the glass in the greenhouse where defective light transmission has occurred) and defect code information indicating the occurrence of defective light transmission at that location, together with measured growth environment information.

The transmission unit 130 transmits, to the environment control server 300, a status message containing at least one among plant growing state information measured by the plant growing state measurement unit 110 and growth environment information measured by the growth environment measurement unit 120. Also, it transmits a message containing information on a location where plant ecology information is acquired or information on a location where growth environment information is acquired. Alternatively, it transmits a message containing information on a location where a defect or a defect code for the defect occurs.

The reception unit 140 receives a message transmitted from the environment control server 300.

The movement unit 150 moves the plant observation device 100 according to a set movement algorithm, or moves the plant observation device 100 while dynamically changing movement direction, distance, etc., based on images of the surroundings captured by the image capture unit 111.

Further, the movement unit 150 may perform a given operation in accordance with an instruction code (e.g., an instruction code by which the environment control server 300 remotely controls the plant observation device 100 to perform an operation of measuring the growing state of a specific plant or an operation of changing the growth environment, for example, opening and closing the door of the greenhouse or changing temperature, humidity, etc., in place of a non-working controller), which is contained in the message the reception unit 140 receives from the environment control server 300.

The plant observation device 100 having such a structure can be implemented in a robotic form, or implemented in such a manner so as to move along rails installed in the measurement area.

Figure 4:
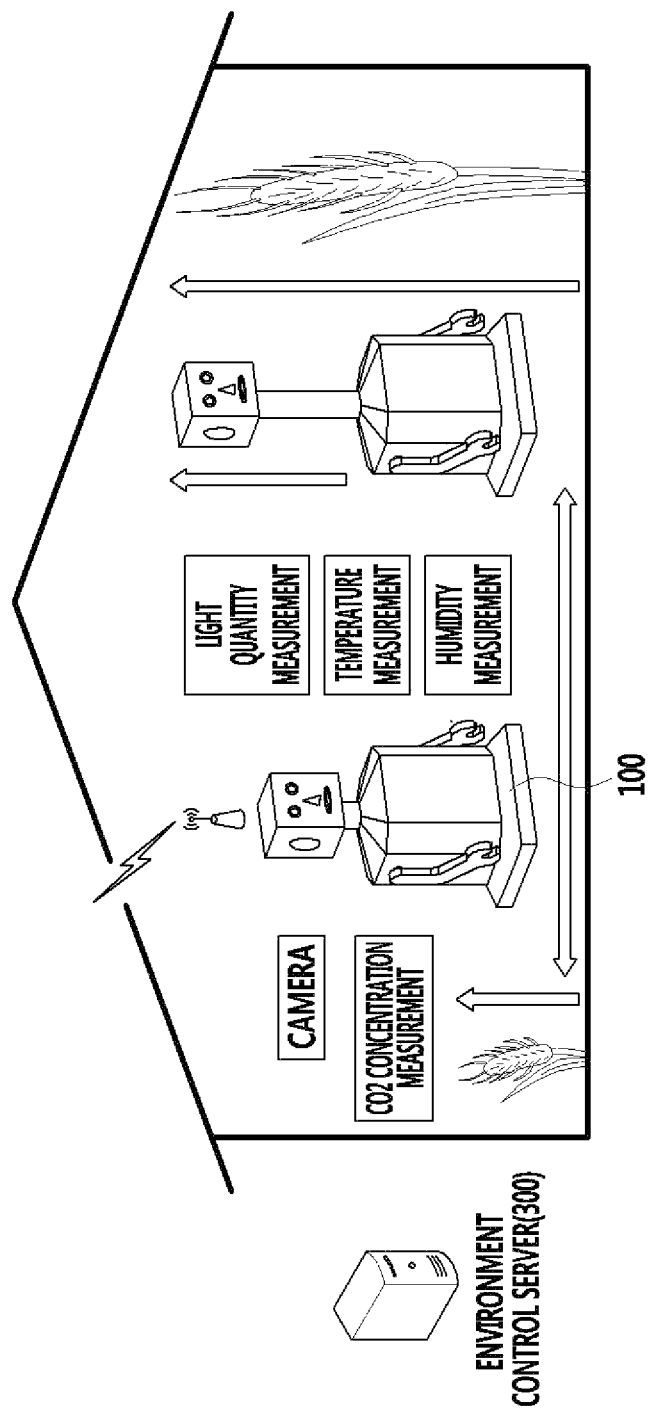
FIG. 4 is an illustration showing the measurement of the growing state and growth environment of plants in a greenhouse using a plant observation device according to an exemplary embodiment of the present invention.

FIG. 4 is an illustration showing the measurement of the growing state and growth environment of plants in a greenhouse using a plant observation device according to an exemplary embodiment of the present invention.

As shown in FIG. 4, the plant observation device 100 according to the exemplary embodiment of the present invention implemented in a robotic form can measure the growing state and growth environment of plants while moving inside the greenhouse.

Next, a plant observation method according to an exemplary embodiment of the present invention will be described with respect to an example in which plant growth monitoring is performed as the plant observation device according to the exemplary embodiment of the present invention operates in such an environment as shown in FIG. 4.

Figure 5:
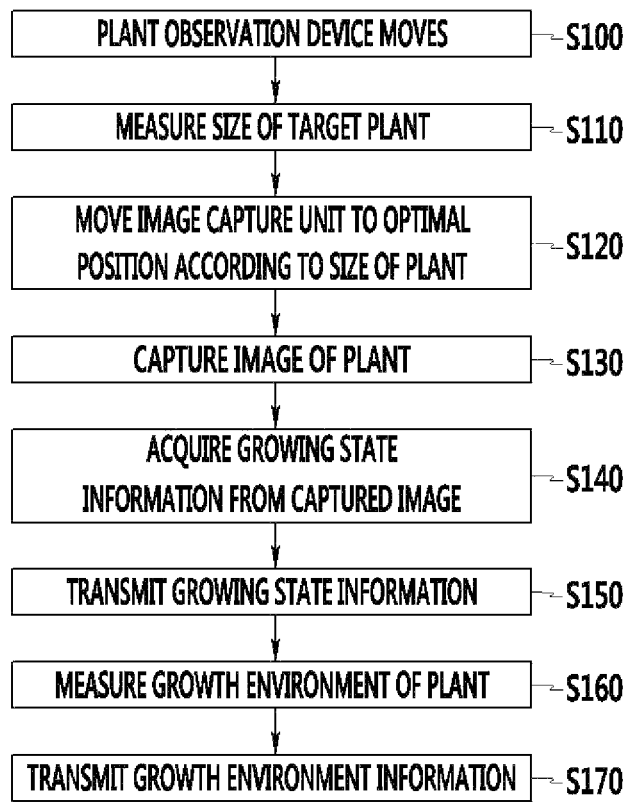
FIG. 5 is a flowchart showing a plant observation method according to an exemplary embodiment of the present invention.

FIG. 5 is a flowchart showing a plant observation method according to an exemplary embodiment of the present invention.

The plant observation device 100 according to the exemplary embodiment of the present invention moves in order to measure the growing state and growth environment of plants in such a greenhouse environment as illustrated in FIG. 4 (S100). For example, the movement unit 150 moves to a target plant in order to measure the growth state of a plant closest to the plant observation device 100, or in order to measure the growth state of a plant which is in a period when measurement is required, based on a previously measured growing state of a plant, or in order to measure the growing state of a certain plant indicated in the message transmitted from the environment control server 300.

When the plant observation device 100 is placed at a target plant, it measures the size of the plant to achieve optimal image capture (S110). Concretely, the plant growing state measurement unit 110 of the plant observation device 100 captures an image of the plant, and measures the size of the plant based on the captured image of the plant. For measurement of the size of the plant, image capture of the plant may be performed while moving the image capture unit 111. For example, the plant image may be captured while moving the image capture unit 111, which is installed to be movable up, down, left, and right within a predetermined distance, upward.

The plant growing state measurement unit 110 places the image capture unit 111 in a position where the growing state of the plant can be optimally captured, based on the size (e.g., plant length) of the plant (S120). For example, the image capture unit 111 is placed in a position corresponding to the tip end of the plant to capture the plant image (S130). The plant growing state measurement unit 110 transmits a captured image to the environment control server 300 through the transmission unit 130, or acquires growing state information from the captured image and transmits the acquired growing state information to the environment control server 300 through the transmission unit 130 (S150). Herein, the plant growing state measurement unit 110 may additional transmit positional information of the measurement location, as well as the captured image of the plant or the growing state information.

The growth environment measurement unit 120 measures the growth environment of the plant to acquire growth environment information containing at least one of the following: temperature, humidity, carbon dioxide, and light quantity (S160), and transmits the acquired growth environment information to the environment control server 300 through the transmission unit 130 (S170). The positional information of the location where the growth environment information is measured can also be additionally transmitted.

The growth environment measurement unit 120 stores growth environment information measured for each location, and later calculates statistical values based on the measured growth environment information for each location. For example, the average temperature in a measurement area, e.g., a greenhouse, is calculated based on the temperature at each location, the average humidity in the greenhouse is calculated based on the humidity in each location, the average amount of carbon dioxide in the greenhouse is calculated based on the amount of carbon dioxide at each location, or the average quantity of light in the greenhouse is calculated based on the quantity of light at each location.

The statistical values calculated as such can be transmitted to the environment control server 300. Based on these statistical values, the temperature or humidity in the entire greenhouse, the amount of carbon dioxide, or the quantity of light can be controlled. Optionally, the temperature, humidity, amount of carbon dioxide, quantity of light, etc. at a particular location can be controlled.

Based on the above-described growing state information and growth environment information of the plant measured by the plant observation device 100 and the location where this information is measured, environmental control can be carried out later by means of the controllers 200a, 200b, and 200c so that the plant grows in an optimum environment. For example, when a need arises to control the temperature in the greenhouse, the measurement area, based on the growing state information and growth environment information, the environment control server 300 transmits a control message to the controller 200b for temperature control so that the controller 200b controls temperature. Also, when a need arises for humidity control, it transmits a control message to the controller 200c for humidity control so that the controller 200c controls humidity. Further, when a need arises for light quantity control, it transmits a control message to the controller 200a for ventilation window control so that the controller 200a controls a ventilation window to adjust the quantity of light entering the greenhouse. The control message contains the identification number and positional information of a related controller. If a control message received by a controller corresponds to the controller itself, that is to say, the control message contains the same identification number as the controller, or the positional information corresponds to the position of the controller, the controller may perform a related operation in accordance with the received control message.

Next, a process for measuring the quantity of light during growth environment measurement according to an exemplary embodiment of the present invention, which is to be carried out as stated above, will be described concretely.

Figure 6:
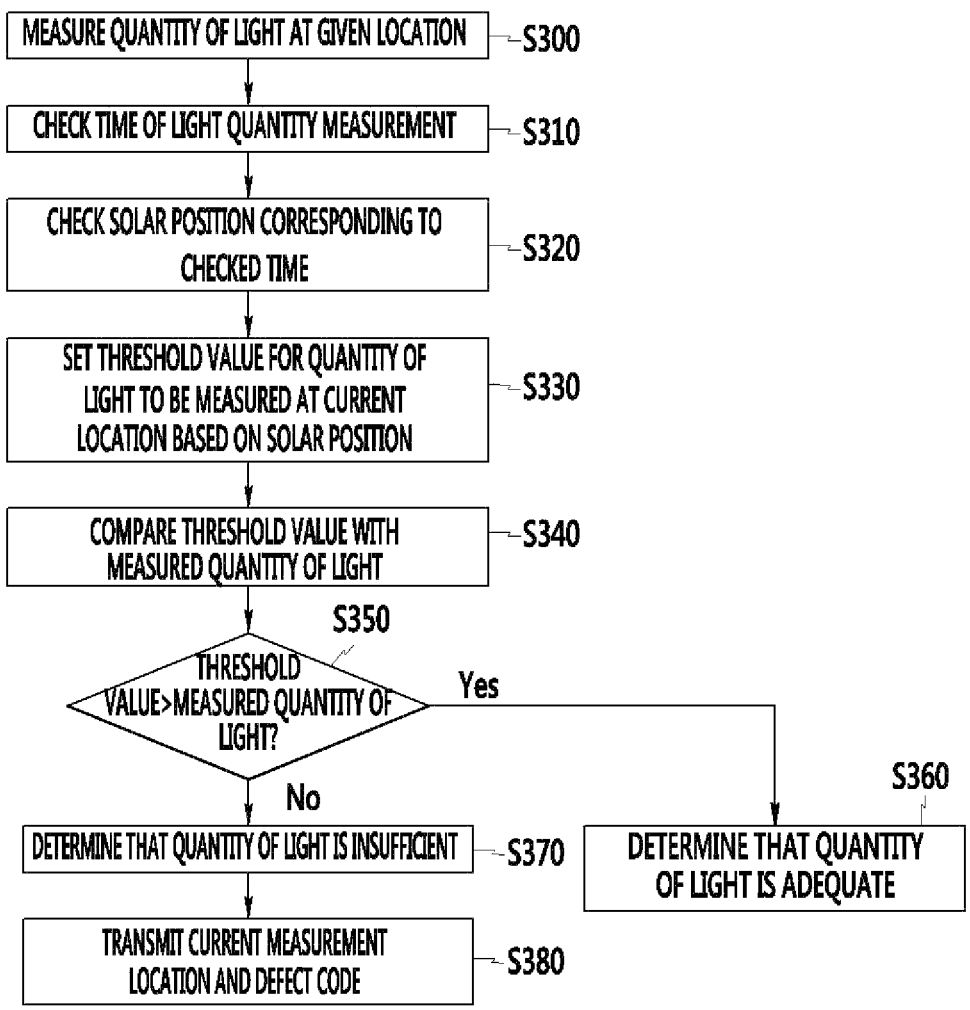
FIG. 6 is a view showing a process for measuring the quantity of light during growth environment measurement when plant observation is performed according to an exemplary embodiment of the present invention.

FIG. 6 is a view showing a process for measuring the quantity of light during growth environment measurement when plant observation is performed according to an exemplary embodiment of the present invention.

The light quantity measuring unit 124 of the movable plant observation device 100 measures the quantity of light at a given location (S300). Also, it checks the time when the current light quantity measurement is made, and checks the solar position at the checked time (S320).

Based on the currently checked solar position, a threshold value for the quantity of light to be measured at the current light quantity measurement location is checked (S330), and the checked threshold value is compared with the measured quantity of light (S340). The solar position for each hour and the threshold value for each measurement location depending on the solar position may be preset, stored, and managed by the light quantity measuring unit 124, or may be provided from an external server, such as the environment control server 300.

If the measured quantity of light is more than the threshold value, it is determined that the quantity of light at the current measurement location that is measured is adequate (S350 and S360). If the measured quantity of light is less than the threshold old value, it is determined that the quantity of light at the current measurement location is insufficient (S370). Once it is determined that the quantity of light is insufficient, the current measurement location and a defect code are transmitted to the environment control server 300 to inform that the quantity of light at that location is insufficient (S380). Alternatively, a message indicating that the quantity of light at that location is insufficient may be transmitted to a mobile terminal (not shown) of the greenhouse administrator, in place of the environment control server 300. At this point, positional information of the glass in the greenhouse corresponding to the measurement location may be additionally transmitted to inform that the light transmitting state of the glass is defective.

In the event of insufficiency in the quantity of light at a given location, it may be determined that something is wrong with the light transmittance of the glass in the greenhouse corresponding to the measurement location, and therefore proper measures (e.g., glass replacement) can be taken.

Moreover, in the plant observation method according to the exemplary embodiment of the present invention, the observation and diagnosis of pests can be performed.

Figure 7:
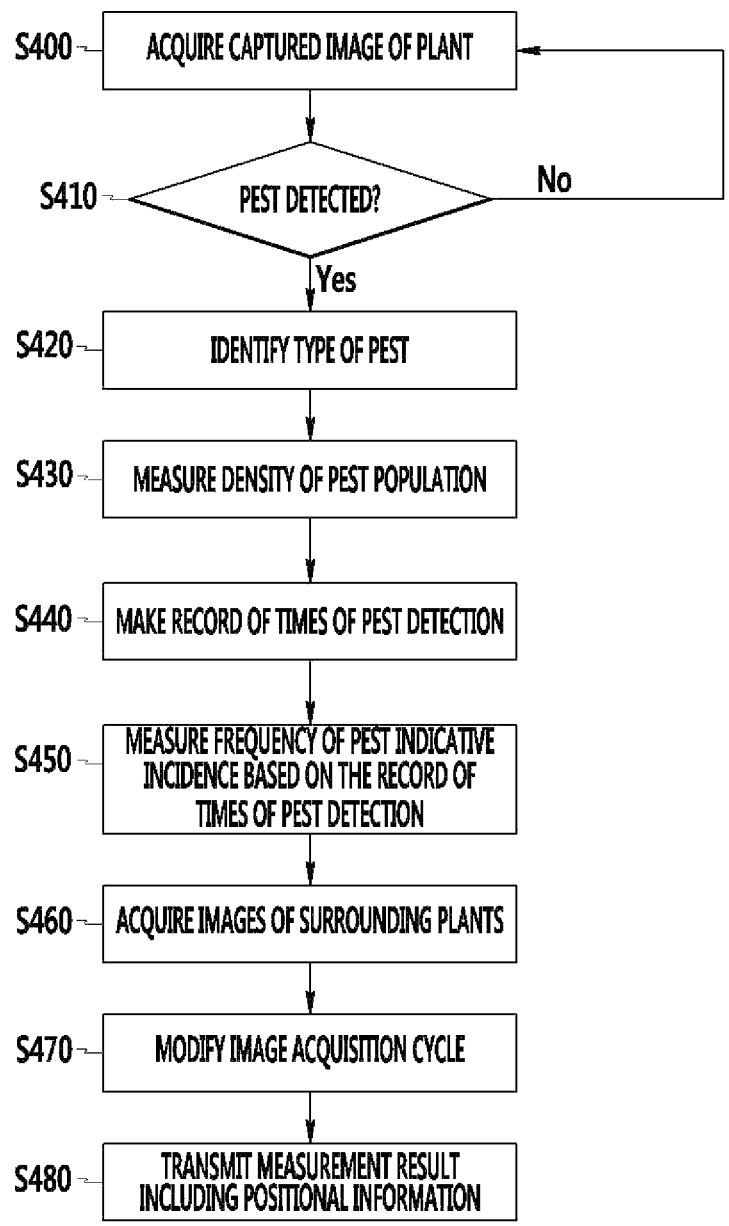
FIG. 7 is a view showing a process for the observation and diagnosis of pests according to an exemplary embodiment of the present invention.

FIG. 7 is a view showing a process for the observation and diagnosis of pests according to an exemplary embodiment of the present invention.

As described above, when the plant observation device 100 moves to a target plant, captures the plant at an optimum position (e.g., a position corresponding to the plant length), and acquires an image of the plant (S400), the plant growing state measurement unit 110 performs pest observation and diagnosis as follows based on the captured image.

The plant growing state measurement unit 110 detects the presence of a pest from the acquired image (S410), and if there is a pest, identifies the type of the pest (S420). For example, the plant growing state measurement unit 110 can detect the pest type by comparing the captured image with previously acquired images of pests for each pest type.

The plant growing state measurement unit 110 measures the density of the pest population in the plant (S430). Then, it makes a record of times when a pest is detected (S440), and measures the incidence of pests indicative of the frequency with which a pest occurs based on the record of times when a pest is detected (S450). Next, images are captured of surrounding plants placed within a set distance from the plant from which the pest is found (S460). At this point, the plant growing state measurement unit 110 can acquire images of surrounding plants within a set distance while moving the plant observation device 100 in connection with the movement unit 150.

Moreover, the plant growing state measurement unit 110 modifies a plant image acquisition cycle based on the detection of a pest (S470). For example, when the plant image acquisition cycle is set to a first cycle to capture images of a plant, it can be changed to a second cycle, which is faster than the first cycle, thereby detecting the spreading situation of pests and quickly taking measures.

Further, the plant growing state measurement unit 110 transmits a pest diagnosis result to the environment control server 300 or the administrator's mobile terminal (not shown) (S480). At this time, positional information of the plant with a pest is also transmitted, so that measures can be taken more quickly. The sequence of the steps S420 through S470 among the steps shown in FIG. 7 is not limited to the sequence shown in FIG. 7 and may be selectively changed.

The above-described plant observation device is able to classify measured growing state information and growth environment information of a plant based on locations and store and manage it in directories. Such stored and managed information as above is transmitted to the environment control server via a wireless network, thus helping to establish an optimum environment for the growth of plants in a greenhouse.

By applying the plant observation device according to the exemplary embodiment of the present invention in the agricultural field, the added value and productivity of plants can be increased, and automated plant production can lead to labor savings.

According to an exemplary embodiment of the present invention, the plant observation device measures the growing state and growth environment of a plant while moving, thereby achieving more accurate observations of the plant.

Because the plant observation device measures environment information and growth information while moving, facility costs incurred in building a sensor for measuring the environment in a greenhouse can be lowered. In addition, accurate growth information including positional information can be collected in real time.

The exemplary embodiments of the present invention may also be implemented by a program realizing functions corresponding to the construction of the embodiment, and a recording medium on which the program is recorded, other than the device and/or method described above. Such implementation may be easily made from the disclosure of the above embodiments by those skilled in the art.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A plant observation device comprising:
   a plant growing state measurement unit that measures the growing state of a plant to acquire growing state information;
   a growth environment measurement unit that measures the growth environment of a measurement area in which the plant is cultivated to acquire growth environment information, measures the quantity of light of the measurement area, and detects a light transmitting state of the measurement area based on the measured quantity of light and the time of light quantity measurement; and
   a transmission unit that transmits the measured growing state information and growth environment information of the plant, and additionally transmits positional information of each location where the growing state information and growth environment information are acquired,
   wherein the plant observation device observes a plant placed at a given location while moving within the measurement area.

2. The plant observation device of claim 1, wherein the plant growing state measurement unit comprises:
   an image capture unit that captures an image of a plant; and
   a capture position adjusting unit that acquires the size of the plant from the captured image of the plant and adjusts the position of the image capture unit based on the acquired size of the plant.

3. The plant observation device of claim 2, wherein the size of the plant represents the length of the plant, and the image capture unit is adjusted to a position corresponding to the tip of the plant, and
   the plant growing state information includes at least one of leaf temperature, leaf moisture, internode length, sclerocauly, chlorophyll content, number of flower sets, number of fruit sets, and fruit color.

4. The plant observation device of claim 1, wherein the growth environment measurement unit further comprises at least one of:
- a light quantity measuring unit for measuring the quantity of light in the measurement area;
- a temperature measuring unit for measuring the temperature in the measurement area;
- a humidity measuring unit for measuring the humidity in the measurement area; and
- a carbon dioxide measuring unit for measuring the concentration of carbon dioxide in the measurement area.

5. The plant observation device of claim 4, wherein the light quantity measuring unit comprises:
- a light quantity measuring module for measuring the quantity of light at a given location of the measurement area;
- a solar position estimation module for estimating a current solar position based on the time of light quantity measurement;
- a threshold value setting module for setting a threshold value for an optimum quantity of light at the light quantity measurement location based on the estimated solar position; and
- a detection module for comparing the threshold value with the measured quantity of light.

6. The plant observation device of claim 5, wherein
if the current measured quantity of light is lower than the threshold value, it is detected that a defect in the quantity of light has occurred at the corresponding location, and
the detection module transmits positional information of the measurement area with the defect and defect code information indicating the occurrence of defective light transmission at the corresponding location.

7. The plant observation device of claim 6, wherein, if the measurement area is a greenhouse, the positional information of the measurement area where the defect has occurred indicates the location of the glass in the greenhouse where the defective light transmission has occurred.

8. The plant observation device of claim 1, further comprising a movement unit that moves the plant observation device in accordance with a set movement algorithm or an instruction code received from the outside,
wherein the movement unit moves the plant observation device while dynamically changing movement direction, distance, etc., based on images captured by the image capture unit.

9. The plant observation device of claim 2, wherein the plant growing state measurement unit detects the presence or absence of a pest based on the captured image, and if there is a pest, performs at least one of identification of the type of the pest, measurement of the density of the pest population in the plant, measurement of the incidence of pests, acquisition of images of surrounding plants, and modification of a plant image acquisition cycle.

10. The plant observation device of claim 1, further comprising a reception unit that receives a message transmitted from an external server,
wherein the plant observation device operates a controller installed in the measurement area to control the growth environment in accordance with an instruction code contained in the control message.

11. A plant observation method, comprising:
acquiring, by a plant observation device, growing state information by measuring a growing state of a plant placed in a measurement area while moving within the measurement area;
creating, by the plant observation device, growth environment information by measuring the growth environment in the measurement area while moving within the measurement area; and
transmitting, by the plant observation device, a status message containing the measured growing state information and growth environment information of the plant and positional information of the measurement area where the information is acquired,
wherein the creating of growth environment information comprises measuring the quantity of light in the measurement area, and detecting a light transmitting state of the measurement area based on the measured quantity of light and the light quantity measurement time.

12. The plant observation method of claim 11, wherein the acquiring of growing state information comprises:
causing the image capture unit to capture an image of the plant;
acquiring the size of the plant from the captured image of the plant;
adjusting the position of the image capture unit based on the acquired size of the plant so that the image capture unit is placed in a position corresponding to the tip of the plant; and
causing the position-adjusted image capture unit to capture an image of the plant and acquiring the growing state information based on the captured image.

13. The plant observation method of claim 11, wherein
the detecting of a light transmitting state further comprises:
measuring the quantity of light at a given location of the measurement area;
estimating the current solar position based on the time of light quantity measurement;
setting a threshold value for an optimum quantity of light at the light quantity measurement location based on the estimated solar position;
comparing the threshold value with the measured quantity of light; and
if the measured quantity of light is lower than the threshold value, detecting that a defect in the quantity of light has occurred at the light quantity measurement location.

14. The plant observation method of claim 13, further comprising transmitting positional information of the measurement area with the defect and defect code information indicating the occurrence of defective light transmission at the corresponding location.

15. The plant observation method of claim 11, wherein the creating of growth environment information further comprises at least one of:
measuring the temperature in the measurement area;
measuring the humidity in the measurement area; and
measuring the concentration of carbon dioxide in the measurement area.

16. The plant observation method of claim 11, further comprising the step in which the plant observation apparatus creates average growth environment information based on growth environment information for each location measured while moving within the measurement area.

17. The plant observation method of claim 11, wherein the positional information contained in the status message includes at least one of information on the location of the measurement area, information on a location where the measured growing state information is acquired, and information on a location where the measured growth environment information is acquired.

18. A plant observation method comprising:

acquiring, by a plant observation device, an image of a plant placed in a measurement area while moving within the measurement area;

detecting the presence or absence of a pest from the image of the plant;

if there is a pest, performing observation and diagnosis of the pest; and transmitting a result of the observation and diagnosis and positional information of the plant from which the pest is detected.

19. The plant observation method of claim 18, wherein the performing of the observation and diagnosis of the pest comprises at least one:

identifying the type of the pest;

measuring the density of the pest population in the plant;

making a record of times of pest detection and measuring the incidence of pests indicative of the frequency with which a pest occurs based on the record of times of pest detection;

acquiring images of surrounding plants placed within a set distance from the plant from which the pest is found;

modifying a plant image acquisition cycle; and transmitting a pest diagnosis result and positional information of the plant from which the pest is detected.

20. The plant observation method of claim 18, wherein the acquiring of an image of a plant comprises:

causing the image capture unit operative to capture an image of the plant;

acquiring the size of the plant from the captured image of the plant;

adjusting the position of the image capture unit based on the acquired size of the plant so that the image capture unit is placed in a position corresponding to the tip of the plant; and causing the position-adjusted image capture unit to capture an image of the plant and acquiring the growing state information based on the captured image.

\* \* \* \* \*